United States Patent [19]

Cereghetti et al.

[11] Patent Number: 5,334,766
[45] Date of Patent: Aug. 2, 1994

[54] PROCESS FOR THE RESOLUTION OF RACEMIC DIPHOSPHINE OXIDES

[75] Inventors: Marco Cereghetti, Basel, Switzerland; Alain Rageot, St. Louis, France

[73] Assignee: Hoffmann-La Roche INc., Nutley, N.J.

[21] Appl. No.: 866,384

[22] Filed: Apr. 9, 1992

[30] Foreign Application Priority Data

Apr. 29, 1991 [CH] Switzerland .................... 1272/91

[51] Int. Cl.$^5$ .................... C07F 9/53; C07F 9/572; C07F 9/655; C07F 9/6553
[52] U.S. Cl. ........................... 568/14; 568/15; 549/6; 549/216; 548/412; 560/86; 560/108; 560/139; 560/141
[58] Field of Search ............... 568/14, 15; 548/412; 549/6, 216; 560/86, 108, 139, 141

[56] References Cited

U.S. PATENT DOCUMENTS 4,306,082 12/1981 Brunner et al. .................... 568/17
4,556,740 12/1985 Hansen et al. .................... 568/13

FOREIGN PATENT DOCUMENTS 104375 8/1983 European Pat. Off. .
398132 5/1990 European Pat. Off. .

OTHER PUBLICATIONS

Org. Synth., vol. 67, 20–30 (1989).
J. Chromatography, 450, (1988), 163–168, Salvadori et al.

Primary Examiner—Marianne M. Cintins
Assistant Examiner—Margaret J. Page
Attorney, Agent, or Firm—George M. Gould; George W. Johnson; Ellen Ciambrone Coletti

[57] ABSTRACT

A process for the resolution of racemic diphosphine oxides into the optically active antipodes by reacting the racemate with a resolving agent comprising using a carbamate or thiocarbamate of an optically active α-hydroxycarboxylic acid or α-aminocarboxylic acid as the resolving agent.

6 Claims, No Drawings

PROCESS FOR THE RESOLUTION OF RACEMIC DIPHOSPHINE OXIDES

BRIEF SUMMARY OF THE INVENTION

The present invention relates to a racemate resolution process and to certain diastereomeric associates which result from this process.

In particular, the present invention relates to a novel process for the resolution of racemic diphosphine oxides into the optically active antipodes by reacting the racemate with a resolving agent. This process comprises using a carbamate or thiocarbamate, preferably a carbamate, of an optically active α-hydroxycarboxylic acid or α-aminocarboxylic acid as the resolving agent. Not only monocarboxylic acids, but also dicarboxylic acids can be used.

The process in accordance with the invention is based on the fact that the respective racemic diphosphine oxide unexpectedly forms two diastereomeric associates of different solubility with the carbamate or thiocarbamate of an α-hydroxycarboxylic acid or α-aminocarboxylic acid which is used. Thereby, in accordance with this process, a variety of racemic diphosphine oxides can be resolved into their optically active antipodes which were not accessible or which were accessible only with difficulty, for example, in very low yields, using previously known resolving agents such as, for example, the (−)-(L)-dibenzoyltartaric acid disclosed in European Patent Specification 15514.

The aforementioned European Patent Specification 15514 describes, inter alia, a process for the resolution of racemic mixtures of phosphine oxides, which is effected according to the principles of enantiomer separation via stereomeric compounds in organic solution. In this known process, an optically pure isomer of a mono- or bisacylated tartaric acid such as, for example, (−)-(L)-dibenzoyltartaric acid monohydrate is used as the resolving agent. It has, however, been found that this process is not suitable, for example, for the resolution of racemic (6,6'-dimethylbiphenyl-2,2'-diyl)-bis-(di-p-tolylphosphine oxide) ("p-TOLBIPHEMPO") with (−)-(L)-dibenzoyl tartaric acid monohydrate. On the contrary, the resolution is successful in accordance with the present invention, for example, using the phenylcarbamate of (−)- or (+)-lactic acid, that is, a resolving agent which previously has not been used for the optical resolution of racemic diphosphine oxides.

DETAILED DESCRIPTION OF THE INVENTION

The present invention relates to a novel process for the resolution of racemic diphosphine oxides into the optically active antipodes by reacting the racemate with a resolving agent. This process comprises using a carbamate or thiocarbamate, preferably a carbamate, of an optically active α-hydroxycarboxylic acid or α-aminocarboxylic acid as the resolving agent. Not only monocarboxylic acids, but also dicarboxylic acids can be used.

The resolution process in accordance with the invention is carried out by reacting the racemic mixture of diphosphine oxides to be resolved with an optically pure (+)- or (−)-isomer of a carbamate or thiocarbamate of an α-hydroxycarboxylic acid or a α-aminocarboxylic acid, conveniently in a suitable organic solvent. Then, the one of the two diastereomeric associates which is more difficulty soluble in the solvent than the other diastereomeric associate is separated, for example, by filtration, and subsequently treated with a base in order to liberate the one optically pure, or largely pure, diphosphine oxide enantiomer. In most cases, the second optically pure or enriched diphosphine oxide enantiomer, which, being the more soluble diastereomeric associate, is present in greater abundance in the solution, can also be isolated by crystallization. Where this method fails, the second enantiomer is liberated by treatment with a base and subsequently a new diasteromeric, now more difficulty soluble, associate is formed with the antipode of the previously used resolving agent and the resolution process is repeated.

In the above explanation of the resolution process, it is assumed that sufficient resolving agent, that is, one molar equivalent of a dicarboxylic acid or two molar equivalents of a monocarboxylic acid per molar equivalent of diphosphine oxide, is used in order to permit the formation of the two diastereomeric associates. Alternatively, of course, half of the molar amount of the resolving agent based on the amount of racemic diphosphine oxide to be resolved can be used, and in this case the more difficulty soluble diastereomeric associate is obtained as a solid. The unreacted, or largely unreacted, diphosphine oxide then remains in the solution as the second antipode. Also in this case the two antipodes can be isolated in a known manner.

The carbamates or thiocarbamates of optically active α-hydroxycarboxylic acids or α-aminocarboxylic acids which can be used as resolving agents in the resolution process of the invention are compounds which have a "nucleus" of the formula

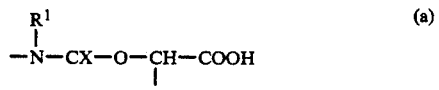

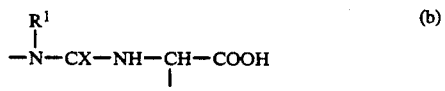

wherein X is oxygen or sulfur and $R^1$ is hydrogen, alkyl or aryl, as well as the ring-condensed derivatives of those carbamates and thiocarbamates defined above which have two carboxy groups and in which $R^1$ is hydrogen. These ring-condensed derivatives are formed by elimination of $H_2O$ between the carboxy group, which is situated in the α-position to the (thio)-carbamoyloxy group, —NH—CX—O—, or (thio)ureido group, —NH—CX—NH—, and the carbamoyl or thiocarbamoyl group itself with ring closure resulting therefrom. They have a "nucleus" of the formula

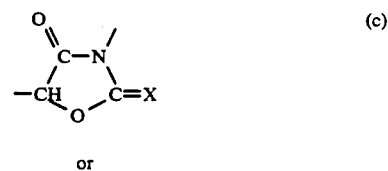

or

-continued

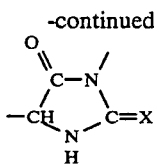

that is, they are 2,4-dioxo-1,3-oxazolidines or 2-thio-4-oxo-1,3-oxazolidines, i.e. "nucleus" (c) wherein X is oxygen or sulfur, and, respectively, 2,4-imidazolidinediones or 2-thio-4-oxoimidazolidines, i.e. "nucleus" (d) wherein X is oxygen or sulfur.

Examples of such resolving agents are the compounds of formulas I–IV hereinafter:

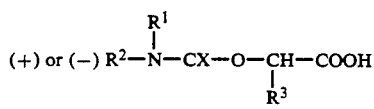

wherein
X and $R^1$ have the significances given above and
$R^2$ is hydrogen, alkyl, aryl-$C_{1-3}$-alkyl or aryl and
$R^3$ is the remaining part of the α-hydroxycarboxylic acid used, with the proviso that one of $R^1$ and $R^2$ is hydrogen;

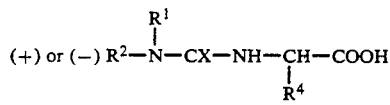

wherein
X, $R^1$ and $R^2$ have the significances given above and
$R^4$ is the remaining part of the α-aminocarboxylic acid used;

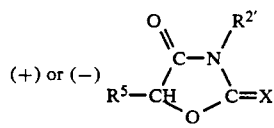

wherein
X has the above significance and
$R^{2'}$ is alkyl, aryl-$C_{1-3}$-alkyl or aryl and
$R^5$ is the remaining part of the α-hydroxycarboxylic acid having two carboxy groups which is used;

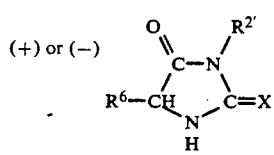

wherein
X and $R^{2'}$ have the significances given above and
$R^6$ is the remaining part of the α-aminocarboxylic acid having two carboxy groups which is used.

The term "alkyl" as used in the meaning of $R^1$, $R^2$, and $R^{2'}$ denotes preferably $C_{1-6}$-alkyl groups. Where $R^1$, $R^2$ or $R^{2'}$ stands for "aryl", either alone or in combination, this is preferably optionally substituted phenyl or naphthyl, whereby as substituents there come into consideration especially $C_{1-6}$-alkyl such as, for example, methyl, ethyl and n-propyl and the like; halogen, preferably fluorine and chlorine; $C_{1-6}$-alkoxy such as, for example, methoxy and ethoxy and the like; and nitro. When substituted, the phenyl or naphthyl group is preferably monosubstituted or disubstituted, whereby in multiply-substituted phenyl or naphthyl, the substituents can be the same or different. Preferred meanings of $R^2$ as aryl-$C_{1-3}$-alkyl are optically active α-phenylethyl, α-phenylpropyl, 1-(α-naphthyl)-ethyl as well as 1-(α-naphthyl)-propyl.

Examples of the term "the remaining part of the α-hydroxycarboxylic acid" as used in $R^3$ or "the remaining part of the α-aminocarboxylic acid" as used in $R^4$ are methyl, phenyl, carboxymethyl, carboxyhydroxymethyl or a group (e) or (f)

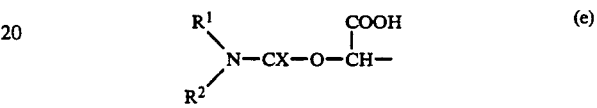

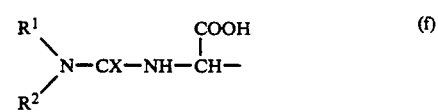

wherein X, $R^1$ and $R^2$ have the significances given above.

The corresponding terms, as used in $R^5$ or $R^6$, denote a group which contains a carboxy group. Examples of such groups are carboxymethyl, carboxyhydroxymethyl, a group (e) and a group (f), as above.

Preferred resolving agents of formulas I–IV are:

The phenylcarbamate of optically active lactic acid, that is, (+)- or (−)-2-phenylcarbamoyloxy-propionic acid of the formula (+)/(−)-$C_6H_5NHCOOCH(CH_3)COOH$;

the phenylcarbamate of optically active mandelic acid, that is, (+)- or (−)-α-phenylcarbamoyloxyphenylacetic acid of the formula (+)/(−)-$C_6H_5NHCOOCH(C_6H_5)COOH$;

the phenylcarbamate of optically active malic acid, that is, (+)- or (−)-2-phenylcarbamoyloxy-succinic acid of the formula (+)/(−)-$C_6H_5NHCOOCH(COOH)CH_2COOH$;

the phenylcarbamate of optically active tartaric acid, that is, (+)- or (−)-2,3-di(phenylcarbamoyloxy)-succinic acid of the formula

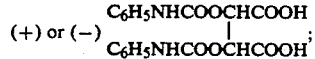

the phenylcarbamate of optically active alanine, that is, (+)- or (−)-2-(3-phenylureido)-propionic acid of the formula (+)/(−)-$C_6H_5NHCONHCH(CH_3)COOH$;

the phenylcarbamate of optically active aspartic acid, that is, (+)- or (−)-2-(3-phenylureido)-succinic acid of the formula (+)/(−)-$C_6H_5NHCONHCH(COOH)CH_2COOH$;

the ring-condensed derivative of the phenylcarbamate of optically active malic acid, that is, (+)- or (−)-5-carboxymethyl-3-phenyl-2,4-dioxo-1,3-oxazolidine of the formula

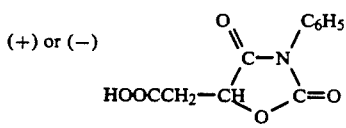

the ring-condensed derivative of the corresponding phenylthiocarbamate, that is, (+)- or (−)-5-carboxymethyl-3-phenyl-2-thio-4-oxo-1,3-oxazolidine of the formula

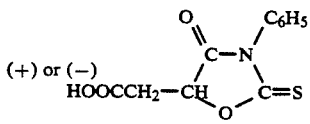

as well as the ring-condensed derivative of the phenylcarbamate of optically active aspartic acid, that is, (+)- or (−)-5-carboxymethyl-3-phenyl-2,4-imidazolidinedione of the formula

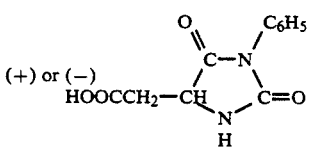

As racemic diphosphine oxides to be resolved, there can be used in accordance with the present invention all such compounds. Examples of such diphosphine oxides are the compounds of the following formulas V and VI, as well as, the further related compounds given hereinafter:

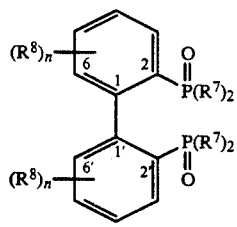

wherein
$R^7$ is alkyl, cycloalkyl, aryl or a five-membered heteroaromatic,
$R^8$ is hydrogen, lower alkyl, lower alkoxy or protected hydroxymethyl and
n is 1, 2, 3 or 4,
with the proviso that both positions 6 and 6′ always carry a substituent $R^8$;
as well as similar diphosphine oxides which are described, for example, in European Patent Publication No. 104,375 (compounds of formula V therein) and European Patent Publication No. 398,132 (compounds of formula III therein);

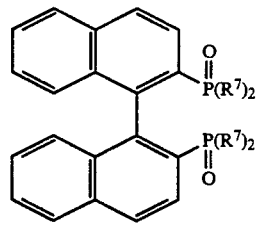

wherein $R^7$ has the significance given above and the naphthalene rings are optionally further substituted.

The terms "alkyl" and "cycloalkyl", as used in the meaning of $R^7$, denote preferably $C_{1-6}$-alkyl and, respectively, $C_{5-7}$-cycloalkyl groups, whereby the alkyl groups can be straight-chain or branched. Where $R^7$ denotes aryl, this is preferably optionally substituted phenyl. Where substituted, such phenyl groups $R^7$ can be substituted in the ortho-, meta- or para-position or also multiply-substituted. As substituents there come into consideration, lower alkyl groups, preferably methyl; lower alkoxy groups, preferably methoxy; di(lower alkyl)amino, preferably dimethylamino; as well as fluorine and chlorine. The term "five-membered heteroaromatic" denotes a substituent of formula (g), (h), (i) or (j):

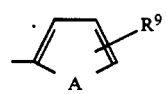
(g)

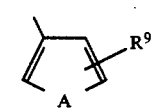
(h)

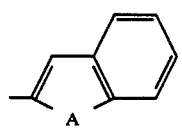
(i)

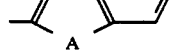
(j)

In these formulas, A is oxygen, sulfur or —$NR^{10}$, $R^9$ is hydrogen, lower alkyl, especially methyl, or lower alkoxy, especially methoxy, and $R^{10}$ is lower alkyl, especially methyl. The terms "lower alkyl" and "lower alkoxy", as used herein, denote straight-chain or branched groups with up to 3 carbon atoms, such as, for example, methyl, ethyl, n-propyl and isopropyl and the corresponding alkoxy groups. As protecting groups for the hydroxymethyl group of $R^8$ there especially come into consideration the usual ether-forming groups, such as, for example, methyl, methoxymethyl and benzyl, as well as ester-forming groups, such as, for example, acetyl and benzoyl.

In the case of formula VI there come into consideration as further substituents on the naphthalene rings, for example, lower alkyl groups, preferably methyl; lower alkoxy groups, preferably methoxy; di(lower alkyl)amino, preferably dimethylamino; as well as fluorine and chlorine.

The following compounds of formulas V and VI are preferred racemic diphosphine oxides in the resolution process of the invention:

Compounds of formula V:
(RS)-(6,6'-Dimethylbiphenyl-2,2'-diyl)-bis-(diphenylphosphine oxide) [named "(RS)-BIPHEMPO"],
(RS)-(6,6'-dimethylbiphenyl-2,2'-diyl)-bis-(di-p-tolylphosphine oxide) [named "(RS)-p-TOLBIPHEMPO"],
(RS)-(6,6'-dimethylbiphenyl-2,2'-diyl)-bis-(dicyclohexylphosphine oxide) [named "(RS)-CyBIPHEMPO"];
(RS)-(6,6'-dimethylbiphenyl-2,2'-diyl)-bis-(di-2-furylphosphine oxide) [named "(RS)-FURBIPHEMPO"];
Compounds of formula VI:
(RS)-2,2'-Bis(diphenylphosphinoxido)-1,1'-binaphthyl [named "(RS)-BINAPO"],
(RS)-2,2'-bis[di(p-tolyl)phosphinoxido]-1,1'-binaphthyl [named "(RS)-p-TOLBINAPO"],
(RS)-2,2'-bis[di(m-tolyl)phosphinoxido]-1,1'-binaphthyl [named "(RS)-m-TOLBINAPO"] and
(RS)-2,2'-bis(dicyclohexylphosphinoxido)-1,1'-binaphthyl [named "(RS)-CyBINAPO"].

The reaction of the racemic diphenylphosphine oxide with the resolving agent, which takes place as the first step in the resolution process, is conveniently effected in an organic or aqueous-organic solvent such as, for example, a lower alkanol, such as, for example, methanol; a di(lower alkyl) ketone, such as, for example, acetone; a lower alkanoic acid ethyl ester, such as, for example, ethyl acetate; an aromatic, such as, for example, toluene; an aqueous-organic solvent, such as, for example, an aqueous lower alkanol, especially aqueous methanol; or an aqueous di(lower alkyl) ketone, especially aqueous acetone; or a mixture of two or more of the aforementioned solvents and/or other organic solvents, such as, for example, a methylene chloride/methanol mixture, an acetone/n-hexane mixture or a toluene/n-hexane mixture. Methanol, ethyl acetate or toluene has been found to be a preferred solvent for this purpose. The reaction is suitably carried out at temperatures between about −20° C. and about +80° C., preferably at about 4° to 25° C. When they are not used in equimolar amounts, the racemic diphosphine oxide and the resolving agents are used in a molar ratio of about 1:2. In most cases, there is obtained a crystallizate of the less soluble associate which can conveniently be separated by filtration or by centrifugation. Should the associate not precipitate by itself, the crystallization can be expedited by the addition of a seeding crystal and/or by cooling. In each case, the reaction conditions and crystallization conditions can be optimized by the planned balancing of the various parameters with one another, for example, choice of solvent, concentration of the two reaction partners in the solvent and temperature, in order to arrive at the desired result.

The subsequent liberation of the diphosphine oxide enantiomer from the separated associate, can be carried out by dissolving or suspending the associate in a water-insoluble organic solvent, such as, for example, methylene chloride, ethyl acetate or toluene, then adding a suitable base in aqueous solution is added to the solution or suspension. Sodium hydroxide, potassium hydroxide, sodium carbonate, potassium carbonate, sodium bicarbonate or potassium bicarbonate is the especially preferred base. Thereby, the thus-formed sodium or potassium salt of the resolving agent, carbamate or thiocarbamate of an optically active α-hydroxycarboxylic acid or α-aminocarboxylic acid, dissolves in the aqueous phase and the resulting liberated diphosphine oxide enantiomer dissolves in the organic phase. The optically active diphosphine oxide can then be isolated from the organic phase in a conventional manner, for example, by concentration under reduced pressure and, if necessary, also at a slightly increased temperature. The optical purity of the diphosphine oxide recovered in this manner is already very high. If desired, the optically purity can be increased to 100% (ee) by repeating the resolution process. In most cases, as the last step to the optically pure enantiomer, the product obtained by concentration can be subjected to a recrystallization.

If desired, the organic solution of the second associate, the other diastereomer, remaining behind after separation of the more difficulty soluble, first associate, can be treated with base and the optically pure or largely pure diphosphine oxide enantiomer can be liberated analogously to the working-up of the first associate described above. Where, however, half of the molar amount of resolving agent is used in the resolution process, the treatment with base does not apply.

The diastereomer associates in accordance with the invention are the immediate products of the resolution process, that is, diastereomeric associates from a (R)- or (S)-diphosphine oxide and a carbamate or thiocarbamate of an optically active α-hydroxycarboxylic acid or α-aminocarboxylic acid. Examples of such associates are those which result from a (R)- or (S)-diphosphine oxide, for example of formula V or VI above, and a resolving agent of formula I, II, III or IV above. Preferred diastereomeric associates are those in which the one component is (R)- or (S)-BIPHEMPO, p-TOLBIPHEMPO, CyBIPHEMPO, FURBIPHEMPO, BINAPO, p-TOLBINAPO, m-TOLBINAPO or CyBINAPO and the second component is (+)- or (−)-2-phenylcarbamoyloxypropionic acid, (+)- or (−)-α-phenylcarbamoyloxy-phenylacetic acid, (+)- or (−)-2-phenylcarbamoyloxy-succinic acid, (+)- or (−)-2,3-di(-phenylcarbamoyloxy)-succinic acid, (+)- or (−)-2-(3-phenylureido)-propionic acid, (+)- or (−)-2-(3-phenylureido)-succinic acid, (+)- or (−)-5-carboxymethyl-3-phenyl-2,4-dioxo-1,3-oxazolidine, (+)- or (−)-5-carboxymethyl-3-phenyl-2-thio-4-oxo-1,3-oxazolidine or (+)- or (−)-5-carboxy-3-phenyl-2,4-imidazolidinedione.

Not only the racemic diphosphine oxides used as starting materials in the resolution process in accordance with the invention, but also the resolving agents used in accordance with the invention are known or can be prepared according to known methods, for example, those described in European Patent Publications Nos. 15,514, 104,375 and 398,132.

The products of the resolution process, that is, the optically active [(R)- or (S)]-diphosphine oxides, can be reduced in a known manner to the corresponding (R)- or (S)-diphosphines. The latter are suitable in the form of their complexes with metals of Group VIII of the periodic system, especially with ruthenium, rhodium, iridium and cobalt, as catalysts in asymmetric hydrogenations and for enantioselective hydrogen displacements in prochiral allylic systems. The production of the (R)- and (S)-diphosphines, their conversion into the complexes and the aforementioned use of the latter are described, for example, in European Patent Publications Nos. 15,514, 104,375 and 398,132.

The following Examples illustrate the invention in more detail. The given enantiomer compositions (ee determination, R/S ratio) are determined in accordance with the CSP-HPLC method described in Org. Synth. 67, 20–30 (1987).

EXAMPLE 1

Racemate resolution of (RS)-(6,6'-dimethylbiphenyl-2,2-diyl)-bis-(dicyclohexylphosphine oxide) [(RS)-CyBIPHEMPO] using (S)-2-phenylcarbamoyloxy-propionic acid 2.0 g (3.3 mmol) of (RS)-CyBIPHEMPO and 1.5 g (7.3 mmol) of (S)-2-phenylcarbamoyloxy-propionic acid are dissolved in 25 ml of a (1:4) mixture of ethyl acetate and n-hexane and the solution is left to stand at +4° C. for about 16 hours. Thereafter, the resulting white, crystalline (S)-CyBIPHEMPO/(S)-2-phenylcarbamoyloxy-propionic acid (1:2)-associate (first crystallizate) [0.7 g; 40% of the theoretical yield based on racemate used; R/S=2.5%/97.5%] is separated by filtration and recrystallized from toluene/ethyl acetate (5:1). In this manner, there is obtained 0.6 g [34.3% of the theoretical yield based on racemate used; R/S=0%/100%] of pure (S)-CyBIPHEMPO/(S)-2-phenylcarbamoyloxy-propionic acid (1:2)-associate, m.p. 197.2° C.; $[\alpha]_{365}^{20}=+179.8°$, $[\alpha]_{436}^{20}=+106.8°$, $[\alpha]_{546}^{20}=+59.9°$, $[\alpha]_{578}^{20}=+52.3°$, $[\alpha]_{589}^{20}=+50.3°$ (c=1.0, CH$_3$OH); infrared spectrum (cm$^{-1}$): 3439, 3299 (—NH, —NH$_2$), 2930, 2653 (aliph. CH), 2496, 2411 (—COOH), 1730 (—COOH), 1708 (carbamate CO), 1541 (CONH), 1220 (ester CO), 770 (trisubst. benzene), 756, 692 (monosubst. benzene); $^1$H-NMR (ppm, CD$_3$OD, 250 MHz): 1.15–2.10 (m, 42x aliph. H), 2.55–2.75 (m, 2x aliph. H), 1.50 (d, J=7.5, 2x CH$_3$), 1.90 (s, 2x CH$_3$), 5.05 (q, J=7.5, 2x aliph. H), 7.05 (m, 2x arom. H), 7.25–7.45 (m, 14x arom. H); mass spectrum: 606 (10,M+), 605 (10,M+—H), 523 (96, M+—C$_6$H$_{11}$), 441 (32, M+—C$_6$H$_{11}$, —C$_6$H$_{10}$), 393 (100, M+—P(O)cyclohexyl$_2$; microanalysis: calc. for C$_{58}$H$_{78}$P$_2$O$_{10}$N$_2$ (1025.229) C 67.95%, H 7.67%, N 2.73%, found C 67.67%, H 7.57%, N 2.67%.

The mother liquor was evaporated under reduced pressure and the residue obtained [2.7 g, R/S=66%/34%] was crystallized from ethyl acetate to give a second crystallizate of associate enriched with (S)-CyBIPHEMPO [0.7 g; 40% of the theoretical yield based on racemated used; R/S=4%/96%].

For the liberation of the (R)-CyBIPHEMPO, the mother liquors are combined and dissolved in 150 ml of ethyl acetate. Then, the organic phase is washed once with 80 ml of saturated aqueous sodium bicarbonate solution and twice with 100 ml of water each time, dried over anhydrous sodium sulphate and evaporated under reduced pressure. The residue [1.3 g, R/S=79%/21%] is dissolved in 25 ml of a (2:1) mixture of ethyl acetate and methylene chloride and the solution is left to stand at room temperature for about 48 hours. The resulting crystallizate [0.9 g; 90% of the theoretical yield based on racemate used; R/S=100%/0%] is separated and the mother liquors are evaporated to dryness [0.3 g; R/S=19.8%/80%].

(S)-CyBIPHEMPO is liberated from the (S)-CyBIPHEMPO/(S)-2-phenylcarbamoyloxy-propionic acid (1:2)-associate in an analogous manner.

EXAMPLE 2

Racemate resolution of (RS)-(6,6'-dimethylbiphenyl-2,2'-diyl)-bis-(diphenylphosphine oxide) [(RS)-BIPHEMPO] using (R,R)-2,3-di(phenylcarbamoyloxy)-succinic acid 5.0 g (8.6 mmol) of (RS)-BIPHEMPO and 3.7 g (9.5 mmol) (R,R)-2,3-di(phenylcarbamoyloxy)-succinic acid, prepared by reacting dibenzyl (RR)-tartrate with phenyl isocyanate and subsequent hydrogenolysis, are dissolved in 64 ml of a 25:7 mixture of ethyl acetate and methanol and the solution is left to stand at room temperature for about 16 hours. The resulting crystallizate is separated and the mother liquor is again brought to crystallization. In this manner, there result a first crystallizate and a second crystallizate of (R)-BIPHEMPO/(R,R)-2,3-di(phenycarbamoyloxy)-succinic acid (1:1)-associate, each of which is separated by filtration [1.6 g; 36.8% of the theoretical yield based on racemate used; R/S=99.9%/0.1%; and 0.6 g; 13.8% of the theoretical yield based on racemate used; R/S=100%/0%]. For analysis, the second crystallizate is dried for 7 hours at 70° C./15 mbar; m.p. 208.7°–210.9° C.; $[\alpha]_{356}^{20}=-185.0°$, $[\alpha]_{436}^{20}=-86.6°$, $[\alpha]_{546}^{20}=-39.8°$, $[\alpha]_{578}^{20}=-33.6°$, $[\alpha]_{589}^{20}=-31.7°$ (c=1.0, CH$_3$OH); infrared spectrum (cm$^{-1}$): 3406, 3319 (—NH, —NH$_2$), 2829, 2794 (—COOH), 1729 (—COOH), 1603 (Ar), 1591 (CONH), 1441 (P-Ar), 1209 (—P=O), 750, 723 (o-disubst. benzene), 692 (monosubst. benzene); $^1$N-NMR (ppm, DMSO, 250 MHz): 1.20 (s, 2x CH$_3$), 5.57 (s, 2H), 6.94–7.80 (m, 36x arom. H), 9.96 (s, 2x NH), 13.7 (bs, 2x, OH); mass spectrum: BIPHEMPO fragmentation pattern, no fragments of the resolving agent; microanalysis: calc. for C$_{56}$H$_{48}$N$_2$O$_{10}$P$_2$ (970.947) C 69.27%, H 4.98%, N 2.89%, found C 68.89%, H 5.18%, N 2.82%.

The mother liquor is evaporated under reduced pressure and the residue obtained [7.0 g, R/S=38.6%/61.4%] is crystallized to give a third crystallizate of associate enriched with (R)-BIPHEMPO [1.7 g, 39.1% of the theoretical yield based on racemate used; R/S=70%/30%].

For the liberation of the (S)-BIPHEMPO, the residue [5.0 g, R/S=15%/85%] obtained from the remaining mother liquor by evaporation under reduced pressure is dissolved in 200 ml of ethyl acetate and the organic phase is washed once with saturated aqueous sodium bicarbonate solution and twice with 150 ml of water each time, dried over anhydrous sodium sulphate and evaporated under reduced pressure. After recrystallization of the residue [2.7 g, R/S=15%/85%] from ethyl acetate, there results crystalline (RS)-BIPHEMPO [1.0 g R/S=49%;/51%] and a mother liquor enriched with (S)-BIPHEMPO [1.7 g, 68% of the theoretical yield based on racemate used, R/S=2.5%/97.5%]. Enantiomer-pure (S)-BIPHEMPO is obtained from this material after a further crystallization from ethyl acetate.

(R)-BIPHEMPO is liberated from the (R)-BIPHEMPO/(R,R)-2,3-di(phenylcarbamoyloxy)-succinic acid (1:1)-associate in an analogous manner.

EXAMPLE 3

Racemate resolution of
(RS)-(6,6'-dimethylbiphenyl-2,2'-diyl)-bis-(di-p-tolyl-phosphine oxide) [(RS)-p-TOLBIPHEMPO] using
(S)-2-phenylcarbamoyloxy-propionic acid 2.7 g (4.1 mmol) of (RS)-p-TOLBIPHEMPO and 2.0 g (9.6 mmol) of (S)-2-phenylcarbamoloxy-propionic acid are dissolved in about 20 ml of hot methanol, a few drops of water are added thereto and the solution is left to stand at room temperature for about 16 hours.

The further procedure is effected analogously to the method described in Example 1 or 2, after which the following products are isolated:

0.7 g of first crystallizate: (S)-p-TOLBIPHEMPO/(S)-2-phenylcarbamoyloxy-propionic acid (1:2)-associate, R/S=6%/94%, m.p. 191°–193° C., $[\alpha]_{586}^{20}$ = +16.8° (c=1.0, CHCl$_3$);

1.0 g of second crystallizate: (S)-p-TOLBIPHEMPO/(S)-2-phenylcarbamoyloxy-propionic acid (1:2)-associate, R/S=25%/75%;

3.0 g of crystallizate from the residue obtained from the mother liquor by evaporation under reduced pressure: (R)-p-TOLBIPHEMPO/(S)-phenylcarbamoyloxy-propionic acid (1:2)-associate, R/S=75%/25%.

Analysis:

(R)-p-TOLBIPHEMPO/(S)-2-phenylcarbamoyloxy-propionic acid (1:2)-associate, 100% ee, m.p. 182°–183° C.; $[\alpha]_{589}^{20}$ = −20° (c=1.0, CHCl$_3$).

(S)-p-TOLBIHEMPO/(S)-2-phenylcarbamoyloxy-propionic acid (1:2)-associated, 100% ee, m.p. 191°–193° C.; $[\alpha]_{589}^{20}$ = −16.8° (c=1.0, CHCl$_3$).

EXAMPLE 4

Racemate resolution of
(RS)-(6,6'-dimethylbiphenyl-2,2'-diyl)-bis-(di-p-tolyl-phosphine oxide) [(RS)-p-TOLBIPHEMPO] using
(S)-2-phenylcarbamoyloxy-propionic acid 3.8 g (6.0 mmol) of (RS)-p-TOLBIPHEMPO and 1.4 g (6.7 mmol) of (S)-2-phenylcarbamoyloxy-propionic acid are dissolved in about 25 ml of warm methanol, about 5 ml of a (4:1) mixture of methanol and water are added thereto and the solution is left to stand at room temperature for about 16 hours.

The further procedure is effected analogously to the method described in Example 1 or 2, after which the following products are isolated;

3.0 g of crystallizate: (S)-p-TOLBIPHEMPO/(S)-2-phenylcarbamoyloxy-propionic acid (1:2)-associate, R/S=25%/75% ;

The (R)-p-TOLBIPHEMPO, R/S=84%/16% is enriched in the residue (2.2 g) remaining after evaporation of the mother liquor.

EXAMPLE 5

Racemate resolution of
(RS)-(6,6'-dimethylbiphenyl-2,2'-diyl)-bis-(di-p-tolyl-phosphine oxide) [(RS)-p-TOLBIPHEMPO] using
(S)-2-phenylcarbamoyloxy-propionic acid 3.8 g (6.0 mmol) of (RS)-p-TOLBIPHEMPO and 2.7 g (13.0 mmol) of (S)-2-phenylcarbamoyloxy-propionic acid are dissolved in about 20 ml of warm methanol, a few drops of water are added thereto and the solution is left to stand at room temperature for about 16 hours.

The further procedure is effected analogously to the method described in Example 1 or 2, after which the following products are isolated:

1.5 g of first crystallizate: (S)-p-TOLBIPHEMPO/(S)-2-phenylcarbamoyloxy-propionic acid (1:2)-associate, R/S=3%/97%;

1:1 g of second crystallizate: (S)-p-TOLBIPHEMPO/(S)-2-phenylcarbamoyloxy-propionic acid (1:2)-associate, R/S=2%/98%;

3.7 g of crystallizate from the residue obtained from the mother liquor by evaporation under reduced pressure: (R)-p-TOLBIPHEMPO/(S)-phenylcarbamoyloxy-propionic acid (1:2)-associate, R/S=86%/14%.

EXAMPLE 6

Racemate resolution of
(RS)-2,2'-bis(diphenylphosphinoxido)-1,1'-binaphthyl [(RS)-BINAPO] using
(S)-2-phenylcarbamoyloxy-propionic acid 1.0 g (1.5 mmol) of (RS)-BINAPO and 0.6 g (3.0 mmol) of (S)-2-phenylcarbamoyloxy-propionic acid are dissolved in about 10 ml of methylene chloride. Then, the solution is treated with some methanol and the methylene chloride is blown off at room temperature under a stream or nitrogen.

The further procedure is effected analogously to the method described in Example 1 or 2, after which the following products are isolated:

0.3 g of crystallizate; (S)-BINAPO/(S)-2-phenylcarbamoyloxy-propionic acid (1:2)-associate, R/S=2%/98%.

1.3 g of crystallizate from the residue obtained from the mother liquor by evaporation under reduced pressure: (R)-BINAPO/(S)-2-phenylcarbamoyloxy-propionic acid (1:2)-associate, R/S=61%/39%.

Analysis:

(R)-BINAPO/(S)-2-phenylcarbamoyloxy-propionic acid (1:2)-associate, 100% ee, m.p. 156°–158° C. (Z), $[\alpha]_{589}^{20}$=118.8° (c=1.0, CHCl$_3$).

(S)-BINAPO/(S)-2-phenylcarbamoyloxy-propionic acid (1:2)-associate, 100% ee.

EXAMPLE 7

Racemate resolution of
(RS)-(6,6'-dimethylbiphenyl-2,2'-diyl)-bis-(diphenyl-phosphine oxide) [(RS)-BIPHEMPO] using
(R)-2,4-dioxo-3-phenyl-5-oxazolidineacetic acid 0.6 g (1.0 mmol) of (RS)-BIPHEMPO and 0.5 g (2.1 mmol) of (R)-2,4-dioxo-3-phenyl-5-oxazolidineacetic acid are dissolved in 40 ml of hot ethyl acetate. The solution is then concentrated and the concentrate is left to stand for about 16 hours.

The further procedure is effected analogously to the method described in Example 1 or 2, after which the following products are isolated:

0.3 g of crystallizate: (R)-BIPHEMPO/(R)-2,4-dioxo-3-phenyl-5-oxazolidineacetic acid (1:2)-associate, R/S=94%/6%;

0.7 g of crystallizate from the residue obtained from the mother liquor by evaporation under reduced pressure: (S)-BIPHEMPO/(R)-2,4-dioxo-3-phenyl-5-oxazolidineacetic acid (1:2)-associate, R/S=36%/64%.

EXAMPLE 8

Racemate resolution of
(RS)-2,2'-bis(diphenylphosphinoxido)-1,1'-binaphthyl
[(RS)-BINAPO] using
(R)-2,4-dioxo-3-phenyl-5-oxazolidineacetic acid 0.8 g (1.2 mmol) of (RS)-BINAPO and 0.6 g (2.6 mmol) of (R)-2,4-dioxo-3-phenyl-5-oxoazolidineacetic acid are dissolved in 50 ml of hot ethyl acetate and the solution is left to stand at room temperature for about 16 hours.

The further procedure is effected analogously to the method described in Example 1 or 2, after which the following products are isolated:

0.7 g of crystallizate: (S)-BINAPO/(R)-2,4-dioxo-3-phenyl-5-oxazolidineacetic acid (1:2)-associate, R/S=10%/89%;

0.7 g of crystallizate from the residue obtained from the mother liquor by evaporation under reduced pressure: (R)-BINAPO/(R)-2,4-dioxo-3-phenyl-5-oxazolidineacetic acid (1:2)-associate, R/S=80%/18%.

Analysis:

(S)-BINAPO/(R)-2,4-dioxo-3-phenyl-5-oxazolidineacetic acid (1:2)-associate 100% ee; m.p. 169°–173° C.; $[\alpha]_{589}^{20}= -120°$ (c=1.0, $CH_3OH$).

(R)-BINAPO/(R)-2,4-dioxo-3-phenyl-5-oxazolidineacetic acid (1:2)-associate 100% ee; m.p. 170°–174° C.; $[\alpha]_{589}^{20}= +144.8°$ (c=1.0, $CH_3OH$).

EXAMPLE 9

Racemate resolution of
(RS)-2,2'-bis(diphenylphosphinoxido)-1,1'-binaphthyl
[(RS)-BINAPO] using
(RR)-2,3-di(phenylcarbamoyloxy)-succinic acid 1.9 g (2.9 mmol) of (RS)-BINAPO and 1.14 g (2.9 mmol) of (RR)-2,3-di(phenylcarbamoyloxy)-succinic acid are dissolved in 100 ml of a hot (4:1) mixture of toluene and n-hexane and the solution is left to stand at room temperature for about 16 hours.

The further procedure is effected analogously to the method described in Example 1 or 2, after which the following products are isolated:

1.3 g of first crystallizate: (S)-BINAPO/(RR)-2,3-di(phenylcarbamoyloxy)-succinic acid (1:1)-associate, R/S=2%/98%;

0.5 g of second crystallizate: (R)-BINAPO/(RR)-2,3-di(phenylcarbamoyloxy)-succinic acid (1:1)-associate, R/S=57%/43%, 1.3 g of crystallizate from the residue obtained from the mother liquor by evaporation under reduced pressure: (R)-BINAPO/(RR)-2,3-di(phenylcarbamoyloxy)-succinic acid (1:1)-associate, R/S=89%/11%.

Analysis:

(S)-BINAPO/(RR)-2,3-di(phenylcarbamoyloxy)-succinic acid (1:1)-associate 100% ee; m.p. 199°–201° C.; $[\alpha]_{589}^{20}= -132°$ (c=1.0, $CH_3OH$).

(R)-BINAPO/(RR)-2,3-di(phenylcarbamoyloxy)-succinic acid (1:1)-associate 100% ee.

EXAMPLE 10

Racemate resolution of
(RS)-2,2'-bis[di(m-tolyl)phosphinoxido]-1,1'-binaphthyl
[(RS)-m-TOLBINAPO] using
(RR)-2,3-di(phenylcarbamoyloxy)-succinic acid 18.6 g (26 mmol) of (RS)-m-TOLBINAPO and 11.62 g (30 mmol) of (RR)-2,3-di(phenylcarbamoyloxy)-succinic acid are dissolved in 154 ml of a (75:2) mixture of ethyl acetate and methanol at 60° C. and the solution is left to stand at room temperature for about 16 hours.

The further procedure is effected analogously to the method described in Example 1 or 2, after which the following products are isolated: 2.4 g of first crystallizate: (S)-m-TOLBINAPO/(RR)-2,3-di(phenylcarbamoyloxy)-succinic acid (1:1)-associate, R/S=2.3%/97.7%;

5.4 g of second crystallizate: (S)-m-TOLBINAPO/(RR)-2,3-di(phenylcarbamoyloxy)-succinic acid (1:1)-associate, R/S=1.5%/98.5%;

6.7 g of third crystallizate: (R)-m-TOLBINAPO/(Rr)-2,3-di(phenylcarbamoyloxy)-succinic acid (1:1)-associate, R/S=83%/17%; 15.7 g of crystallizate from the residue obtained from the mother liquor by evaporation under reduced pressure: (R)-m-TOLBINAPO/(RR)-2,3-di(phenylcarbamoyloxy)-succinic acid (1:1)-associate, R/S=60%/40%.

For the liberation of the (S)-m-TOLBINAPO, the first crystallizate and the second crystallizate are combined (7.8 g), dissolved in 300 ml of methylene chloride, the solution is washed once with 3N aqueous sodium hydroxide solution and three times with 100 ml of water each time, dried over anhydrous sodium sulphate and evaporated under reduced pressure. The residue (5.4 g) is dissolved in the smallest amount of ethyl acetate as possible, the solution is diluted with 50 ml of n-hexane and the diluted solution is left to stand at −20° C. for 3 days. The resulting white crystallizate (4.2 g, 45% of the theoretical yield based on racemate employed; R/S=0.7%/99.3%) is separated; it consists of almost pure (S)-m-TOLBINAPO, $\alpha_D = -224.8°$ (c=1.0, $CHCl_3$). The mother liquor is evaporated to dryness, whereby there is obtained 0.8 g of residue (8.6% of the theoretical yield based on racemate used; R/S=2.7%/97.3%).

EXAMPLE 11

Racemate resolution of
(RS)-(6,6'-dimethylbiphenyl-2,2'-diyl)-bis-(diphenylphosphine oxide) [(RS)-BIPHEMPO] using
(RR)-2,3-di(phenylcarbamoyloxy)-succinic acid 5.0 g (8.6 mmol) of (RS)-BIPHEMPO and 3.7 g (9.5 mmol) of (RR)-2,3-di(phenylcarbamoyloxy)-succinic acid are dissolved in a mixture of 50 ml of ethyl acetate and 14 ml of methanol and the solution is left to stand at room temperature for about 18 hours.

The further procedure is effected analogously to the method described in Example 1 or 2, after which the following products are isolated:

1.7 g of first crystallizate: (R)-BIPHEMPO/(RR)-2,3-di(phenylcarbamoyloxy)-succinic acid (1:1)-associate, R/S=100%/0%;

0.5 g of second crystallizate: (R)-BIPHEMPO/(RR)-2,3-di(phenylcarbamoyloxy)-succinic acid (1:1)-associate, R/S=99.6%/0.4%;

6.5 g of crystallizate from the residue obtained from the mother liquor by evaporation under reduced pressure: (S)-BIPHEMPO/(RR)-di(phenylcarbamoyloxy)-succinic acid (1:1)-associate, R/S=33%/67%.

Analysis:

(R)-BIPHEMPO/(RR)-2,3-di(phenylcarbamoyloxy)-succinic acid (1:1)-associate, 100% ee; m.p. 214°–215° C.; $[\alpha]_{589}^{20}= -31.4°$ (c=1,0, $CH_3OH$).

(S)-BIPHEMPO/(RR)-2,3-di(phenylcarbamoyloxy)-succinic acid (1:1)-associate, 100% ee.

EXAMPLE 12

Racemate resolution of (RS)-2,2'-bis(diphenylphosphinoxido)-1,1'-binaphthyl [(RS)-BINAPO] using (S)-2-(3-phenylureido)-propionic acid 1.44 g (2.2 mmol) (RS)-BINAPO and 0.9 g (4.4 mmol) of (S)-2-(3-phenylureido)-propionic acid are dissolved in about 50 ml of a mixture of methylene chloride, methanol and ethyl acetate, the solution is concentrated to about 30 ml and left to stand at room temperature for about 18 hours.

The further procedure is effected analogously to the method described in Example 1 or 2, after which the following products are isolated:

0.8 g of crystallizate: (R)-BINAPO/(S)-2-(3-phenylureido)-propionic acid (1:2)-associate, R/S=95%/5%;

1.5 g of crystallizate from the residue obtained from the mother liquor by evaporation under reduced pressure: (S)-BINAPO/(S)-2-(3-phenylureido)-propionic acid (1:2)-associate, R/S=26%/74%.

Analysis:

(R)-BINAPO/(S)-2-(3-phenylureido)-propionic acid (1:2)-associate, 100% ee, m.p. 125°–129° C., $[\alpha]_{589}^{20} = +180.6°$ (c=0.5, $CH_3OH$)

(S)-BINAPO/(S)-2-(3-phenylureido)-propionic acid (1:2)-associate, 100% ee.

We claim:

1. A process for the resolution of racemic diphosphine oxides into the optically active antipodes by reacting the racemic diphosphine oxide with a resolving agent, which process comprises using a carbamate or thiocarbamate of an optically active α-hydroxycarboxylic acid or α-aminocarboxylic acid as the resolving agent.

2. A process according to claim 1, wherein the resolving agent is a compound of formula I, $$(+) \text{ or } (-) \quad R^2-\overset{R^1}{\underset{|}{N}}-CX-O-\overset{|}{\underset{R^3}{CH}}-COOH \qquad I$$

wherein

X is oxygen or sulfur, $R^1$ is hydrogen, alkyl or aryl, $R^2$ is hydrogen, alkyl, aryl-$C_{1-3}$-alkyl or aryl and $R^3$ is the remaining part of the α-hydroxycarboxylic acid used, with the proviso that one of $R^1$ and $R^2$ is hydrogen;

formula II

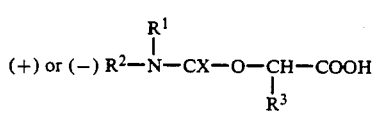

wherein

X, $R^1$ and $R^2$ have the significances given above and $R^4$ is the remaining part of the α-aminocarboxylic acid used;

formula III

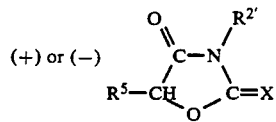

wherein

X has the above significance and $R^{2'}$ is alkyl, aryl-$C_{1-3}$-alkyl or aryl and $R^5$ is the remaining part of the α-hydroxycarboxylic acid used having two carboxy groups;

or formula IV

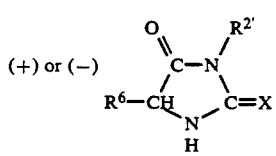

wherein

X and $R^{2'}$ have the significances given above and $R^6$ is the remaining part of the α-aminocarboxylic acid used having two carboxy groups.

3. A process according to claim 2, wherein the resolving agent is (+)- or (−)-2-phenylcarbamoyloxy-propionic acid, (+)- or (−)-α-phenylcarbamoyloxy-phenylacetic acid, (+)- or (−)-2-phenylcarbamoyloxy-succinic acid, (+)- or (−)-2,3-di(phenylcarbamoyloxy)-succinic acid, (+)- or (−)-2-(3-phenylureido)-propionic acid, (+)- or (−)-2-(3-phenylureido)-succinic acid, (+)- or (−)-5-carboxymethyl-3-phenyl-2,4-dioxo-1,3-oxazolidine, (+)- or (−)-5-carboxymethyl-3-phenyl-2-thio-4-oxo-1,3-oxazolidine or (+)- or (−)-5-carboxymethyl-3-phenyl-2,4-imidazolidinedione.

4. A process according to any one of claims 1 to 3, wherein the diphosphine oxide to be resolved is a compound of formula V

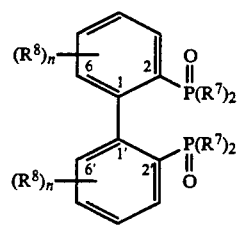

wherein $R^7$ is alkyl, cycloalkyl, aryl or a five-membered heteroaromatic, $R^8$ is hydrogen, lower alkyl, lower alkoxy or protected hydroxymethyl and n is 1, 2, 3 or 4, with the proviso that both positions 6 and 6' always carry a substituent $R^8$; of formula VI

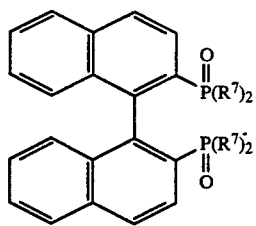

wherein R[7] has the significance given above and the naphthalene rings are unsubstituted or substituted.

5. A process according to claim 4, wherein the racemic diphosphine oxide to be resolved is selected from the group consisting of (RS)-(6,6'-dimethylbiphenyl-2,2'-diyl)-bis-(diphenylphosphine oxide),
(RS)-(6,6'-dimethylbiphenyl-2,2'-diyl)-bis-(di-p-tolylphosphine oxide),
(RS)-(6,6'-dimethylbiphenyl-2,2'-diyl)-bis-(dicyclohexylphosphine oxide),
(RS)-(6,6'-dimethylbiphenyl-2,2'-diyl)-bis-(di-2-furylphosphine oxide),
(RS)-2,2'-bis(diphenylphosphinoxido)-1,1'-binaphthyl,
(RS)-2,2'-bis[di(p-tolyl)phosphinoxido]-1,1'-binaphthyl,
(RS)-2,2'-bis(di(m-tolyl)phosphinoxido)-1,1'-binaphthyl and
(RS)-2,2'-bis(dicyclohexylphosphinoxido)-1,1'-binaphthyl.

6. The process according to claim 5, wherein the racemic diphosphine oxide to be resolved is (RS)-2,2'-bis[di(m-tolyl) phosphinoxido]-1,1'-binaphthyl and the resolving agent is (RR)-2,3-di(phenylcarbamoyloxy)-succinic acid.

* * * * *